US009439605B2

(12) United States Patent
Schäfer et al.

(10) Patent No.: US 9,439,605 B2
(45) Date of Patent: Sep. 13, 2016

(54) C-ARM SYSTEM WITH EXTENDED FIELD OF VIEW

(71) Applicant: KONINKLIJKE PHILIPS N.V., Eindhoven (NL)

(72) Inventors: Dirk Schäfer, Hamburg (DE); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 94 days.

(21) Appl. No.: 14/356,899

(22) PCT Filed: Nov. 9, 2012

(86) PCT No.: PCT/IB2012/056306
§ 371 (c)(1),
(2) Date: May 8, 2014

(87) PCT Pub. No.: WO2013/068987
PCT Pub. Date: May 16, 2013

(65) Prior Publication Data
US 2014/0321612 A1    Oct. 30, 2014

Related U.S. Application Data

(60) Provisional application No. 61/558,539, filed on Nov. 11, 2011.

(51) Int. Cl.
*A61B 6/00* (2006.01)
*A61B 6/02* (2006.01)
*A61B 6/03* (2006.01)

(52) U.S. Cl.
CPC .............. *A61B 6/022* (2013.01); *A61B 6/032* (2013.01); *A61B 6/4441* (2013.01)

(58) Field of Classification Search
CPC ..... A61B 6/022; A61B 6/032; A61B 6/4441
See application file for complete search history.

(56) References Cited

U.S. PATENT DOCUMENTS

6,582,120 B2    6/2003    Schomberg
2005/0084147 A1    4/2005    Groszmann
(Continued)

*Primary Examiner* — David J Makiya
*Assistant Examiner* — Dani Fox (57) ABSTRACT

The present invention relates to a C-arm X-ray imaging system. In order to provide C-arm systems with an extended three-dimensional field of view, a C-arm X-ray imaging system (10), provided to acquire extended three-dimensional images of an object, is provided, comprising a C-arm structure (12) with an X-ray source (14) and an X-ray detector (16) mounted across from the X-ray source, a motorized drive (22) for a rotational movement of the C-arm structure, and a control unit (26). The C-arm structure is provided to perform a rotational scan around an axis of rotation and around an ISO-center acquiring a number of X-ray projections in order to generate image data for a reconstructed three-dimensional field of view. The control unit is configured to control the motorized drive, and to cause the rotational movement of the C-arm structure to perform a first rotational X-ray scan (50) around a first ISO-center (56) with a first axis of rotation for a first field of view, and to perform at least a second rotational X-ray scan (60) around a second ISO-center (62) with a second axis of rotation for a second field of view. The first and the second center of rotation are displaced in relation to each other such that a connection line between the first and the second ISO-center is arranged transverse to the first and the second axis of rotation.

17 Claims, 5 Drawing Sheets

(56) References Cited

U.S. PATENT DOCUMENTS

2006/0039537 A1 2/2006 Strobel
2008/0037712 A1 2/2008 Klingenbeck-Regn
2008/0075225 A1 3/2008 Kalender
2008/0089468 A1 4/2008 Heigl et al.
2011/0255657 A1 10/2011 Noorhoek

C-ARM SYSTEM WITH EXTENDED FIELD OF VIEW

CROSS-REFERENCE TO PRIOR APPLICATIONS

This application is the U.S. National Phase application under 35 U.S.C. §371 of International Application Serial No. PCT/IB2012/056306, filed on Nov. 9, 2012, which claims the benefit of U.S. Application Ser. No. 61/558,539, filed on Nov. 11, 2011. These applications are hereby incorporated by reference herein.

FIELD OF THE INVENTION

The present invention relates to a C-arm X-ray imaging system, a method for acquiring 3D X-ray image data of an object, as well as to a computer program element and a computer readable medium.

BACKGROUND OF THE INVENTION

In a C-arm system, the three-dimensional field of view is limited by the geometrical arrangement of the distance between source and detector and the detector size itself. For imaging procedures on a C-arm system providing tomographic X-ray image data, which procedures are also referred to as CT-like imaging procedures, this limitation is of disadvantage when the area of interest is not completely covered by the three-dimensional field of view. For example, in operational interventions in relation with the liver, for example in hypervascular liver lesion treatment, the region of interest may not be fully covered by the three-dimensional field of view. US 2011/0255657 A1 relates to CT image acquisition and describes the lateral displacement of a detector to increase the 3D field of view. However, the detector has to be provided to be shiftable, requiring mechanical means to allow the displacement.

SUMMARY OF THE INVENTION

Thus, there is a need to provide C-arm systems with an extended three-dimensional field of view requiring reduced mechanical effort.

The object of the present invention is solved by the subject-matter of the independent claims, wherein further embodiments are incorporated in the dependent claims.

It should be noted that the following described aspects of the invention apply also to the C-arm X-ray imaging system, the method for acquiring 3D X-ray image data of an object, as well as for the computer program element and the computer readable medium.

According to a first aspect of the present invention, a C-arm X-ray imaging system, provided to acquire extended three-dimensional images of an object, is provided, comprising a C-arm structure with an X-ray source and an X-ray detector mounted across from the X-ray source, a motorized drive for a rotational movement of the C-arm structure, and a control unit. The C-arm structure is provided to perform a rotational scan around an axis of rotation and around an ISO-centre acquiring a number of X-ray projections in order to generate image data for a reconstructed three-dimensional field of view. The control unit is configured to control the motorized drive. The control unit is also configured to cause the rotational movement of the C-arm structure to perform:
a first rotational X-ray scan around a first ISO-centre with a first axis of rotation for a first field of view; and
at least a second rotational X-ray scan around a second ISO-centre with a second axis of rotation for a second field of view.

The first and the second ISO-centre are displaced in relation to each other such that a connection line between the first and the second ISO-centre is arranged transverse to the first and the second axis of rotation.

The term "transverse" refers to a connection line, which is a straight line, and which is running lateral to the first and the second axis of rotation, i.e. in a cross-wise manner to the first and the second axis of rotation.

For example, the first and the second axis of rotation are displaced such that the first and the second field of view are close to each other or close-by, e.g. as adjacent fields of view.

For example, the first and the second axis of rotation are displaced by parallel shifting. The connection line is then perpendicular to the first and second axis of rotation.

For example, the first and the second axis of rotation are displaced by a transverse shifting, wherein the shifting is having a first perpendicular vector component perpendicular to the two axes of rotation, and a first parallel vector component parallel to the two axes.

For example, the first and the second axis of rotation are displaced by a transverse shifting, wherein the shifting is having a first perpendicular vector component perpendicular to one of the two axes, and a second perpendicular vector component perpendicular to the other one of the two axes.

For example, a combination of a first and a second perpendicular vector component with a parallel vector component is provided.

The first and the second axis of rotation may also be displaced by rotation.

The first and the second axis of rotation may also be displaced by a shifting parallel and/or perpendicular to one of the two axes and by a rotation.

It is noted that the term "C-arm" relates to a system wherein an X-ray source is arranged opposite to an X-ray detector and an object can be arranged between the source and the detector. Source and detector can be moved around the object together, e.g. each rotating in a rotational manner on an arc. Thus, the term "C-arm" also refers to so-called O-arm systems, wherein the two arms of a "C" are closed to form an "O". The term "C-arm" also comprises systems where source and detector are mounted to individual robotic arms which are configured to provide a movement like in a C-arm.

For the first and second rotational scans, the C-arm has a fixed ISO-centre. The displacement (e.g. shift and/or rotation) of the first and the second centre of rotation is provided either by a displacement of an object support in relation to the C-arm structure, or by a displacement of the C-arm structure in relation to the object support. However, for the displacement, a combination of a displacement of both the C-arm structure and the object support in relation to each other may be provided.

For example, the first and second rotational X-ray scans are provided with a number of X-ray projections, which each have a beam with a fan-shaped form in the plane of rotation covering a first, respectively second, volume of projection for reconstructing a first, respectively second, three-dimensional field of view.

For example, the reconstructed three-dimensional field of view has the shape of a cylinder.

For example, the control unit is configured to cause the rotational movement of the C-arm structure to perform a further rotational X-ray scan in addition to the first and second rotational X-ray scan.

According to an exemplary embodiment, the C-arm structure is configured to perform the first rotational X-ray scan with a first trajectory, and the second rotational X-ray scan with a second trajectory displaced to the first trajectory, wherein the first and the second trajectory have the same trajectory shape.

According to an exemplary embodiment, the control unit is configured to cause the rotational movement of the C-arm structure to perform the rotational scans such that the first and the second field of view contact each other.

For example, the first and second fields of view have at least one voxel in common.

For example, the first and the second field of view touch or overlap each other.

According to an exemplary embodiment, the first and second axis of rotation are displaced parallel to each other such that the connection line between the first and the second ISO-centre is arranged perpendicular to the first and the second axis of rotation.

The terms "parallel" and "perpendicular" refer also to an arrangement of the first and the second axes that comprises deviations, e.g. small deviations, from exact parallelism and exact 90°, such as for example ±5° or ±10°.

According to a further exemplary embodiment, the C-arm structure is provided to perform the first and the second rotational scans as a circular arc respectively.

The rotation may be performed with a varying distance of source and/or detector to the centre of rotation, resulting in an elliptically shaped arc, for example.

According to a further example, the control unit is configured to cause the rotational movement of the C-arm structure to perform the first and the at least second rotational scan over at least 140°, for example over 180° plus fan-angle.

Thus, a high degree of reconstruction preciseness can be achieved.

According to a further exemplary embodiment, the control unit is configured to provide a convex hull as an extended three-dimensional field of view enclosing the first field of view and the second field of view and residual regions, which residual regions are located inside the convex hull, but outside the first and second fields of view. The control unit is configured to use projection data from the first rotational X-ray scan for a reconstruction of the first field of view, and projection data from the second rotational X-ray scan for a reconstruction of the second field of view. The control unit is configured to use projection data from at least one part of the first field of view and projection data from at least one part of the second field of view for a reconstruction of the residual regions.

According to an exemplary embodiment, the control unit is configured to use projection data from voxel-covering segments for reconstructing a voxel inside the residual regions, wherein the voxel-covering segments are segments of the first and/or second rotational X-ray scans, which segments comprise acquisition points for which the voxel that is to be reconstructed is located inside the respective first and/or second field of view of the particular acquisition point.

According to a second aspect of the present invention, a method for acquiring 3D X-ray image data of an object is provided, comprising the following steps:

a) Performing a first rotational X-ray scan around a first ISO-centre.
b) Performing at least a second rotational X-ray scan around a second ISO-centre.

The first and the second centre of rotation are displaced in relation to each other such that a connection line between the first and the second ISO-centre is arranged transverse to the first and the second axis of rotation.

The term "field of view" is also referred to as "volume of projection". The field of view, or volume of projection, refers to voxels which are visible in each of the X-ray projection of the respective rotational scan, wherein visible means to be detectable by the detector.

For example, the arc is performed as a circular arc, for example provided as a semicircle over 180° plus the fan angle.

According to an exemplary embodiment, a convex hull is provided as an extended three-dimensional field of view enclosing the first field of view and the second field of view and residual regions, which are located inside the convex hull, but outside the first and second fields of view. For a reconstruction of the first field of view, projection data from the first rotational X-ray scan is used; and, for a reconstruction of the second field of view, projection data from the second rotational X-ray scan is used. For a reconstruction of the residual regions, projection data from at least one part of the first field of view and projection data from at least one part of the second field of view is used.

According to an exemplary embodiment, for reconstructing a voxel inside the residual regions, projection data from voxel-covering segments is used. The voxel-covering segments are segments of the first and/or second rotational X-ray scans, which segments comprise acquisition points for which the voxel that is to be reconstructed is located inside the respective first and/or second field of view of the particular acquisition point.

According to a further exemplary embodiment, for reconstructing a voxel inside the residual regions, differentiated back-projected projection data along the voxel-covering segments is used.

For example, an optimum set-up can be achieved by providing that the first and second rotational X-ray scans are having the same trajectory shape; and that i) the first and the second ISO-centre are displaced such that the first and second field of view contact each other; ii) the first and second axis of rotation are displaced parallel to each other such that the connection line between the first and the second ISO-centre is arranged perpendicular to the first and the second axis of rotation; and iii) the first and the second rotational scans are performed as a circular arc respectively.

However, it must be noted that also deviations and variations from these are provided, as explained. For example, by not fulfilling, or adapting one or more of these parameters, results for an extended field of view may be achieved with a slightly decreased quality, but still valuable for the purposes according to the present invention.

According to an aspect of the present invention, an extended field of view (XFOV) is based on two separate acquisitions, which are each provided in form of a rotational scan around a fixed centre of rotation, i.e. an ISO-centre. However, the at least two acquisition runs, i.e. their centre of rotation, are displaced to each other, thus covering a larger area with scans from different viewing directions providing sufficient image data for a reconstruction. Those areas sufficiently covered by the respective rotational scan are reconstructed based on the particular respective rotational scan. For the residual areas within a convex hull, image data is used from both rotational scans in the following way: As long as the respective voxel, i.e. image point, is covered by a view from one of the rotational scans, i.e. from a respective segment of the rotational scan or trajectory, this image data is used for reconstruction for a larger volume. As soon as the respective voxel is not covered anymore by a next view on the respective trajectory, image data from the other trajectory, or rotational scan, is used, as the voxel is now seen by this respective view. In case of a displacement, in which the three-dimensional fields of view of the rotational X-ray scans do not contact each other, voxels may occur that are neither covered by one of the respective rotational X-ray scans. In such case, the reconstruction may nevertheless be performed, although resulting in a lower degree of preciseness, however, still sufficient enough to provide three-dimensional image data for an extended field of view. However, when the three-dimensional fields of view are contacting each other, and in case of a rotational scan over at least 180° plus fan angle, it is ensured that all voxels inside the convex hull can be reconstructed by a combination of acquired data from the different rotational X-ray scans. The areas inside the three-dimensional fields of view may be reconstructed, for example, with sequential standard FDK reconstructions (a known reconstructing algorithm by Feldkamp, Davis and Kress). However, the three-dimensional fields of view may suffer from truncation artefacts. For example, a circular back projection filtration algorithm (BPF) can be modified such that not only the three-dimensional fields of view, but also the residual regions can be reconstructed. For example, a voxel in the residual regions can be reconstructed using the differentiated back-projected projection data (DBP) along the voxel-covering segments of the trajectories. Thus, a mathematically exact reconstruction is provided in the central plane of the entire field of view if the object fits along the lateral direction into the extended field of view.

These and other aspects of the invention will become apparent from and will be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

As indicated above, the present invention proposes an acquisition and reconstruction method to realize an extended field of view (XFOV) from two arc acquisitions, for example from two circular arc acquisitions. The invention comprises two or more arc acquisitions, for example circular arc acquisitions, with a displaced, for example shifted, ISO-centre between the acquisitions, wherein the first and the second ISO-centre are displaced in relation to each other such that a connection line between the first and the second ISO-centre is arranged transverse to the first and the second axis of rotation. The ISO-centre displacement, e.g. shift can be realized either by a displacement of the whole C-arm system or by displacing the patient table, or by a combination of both.

Figure 1:
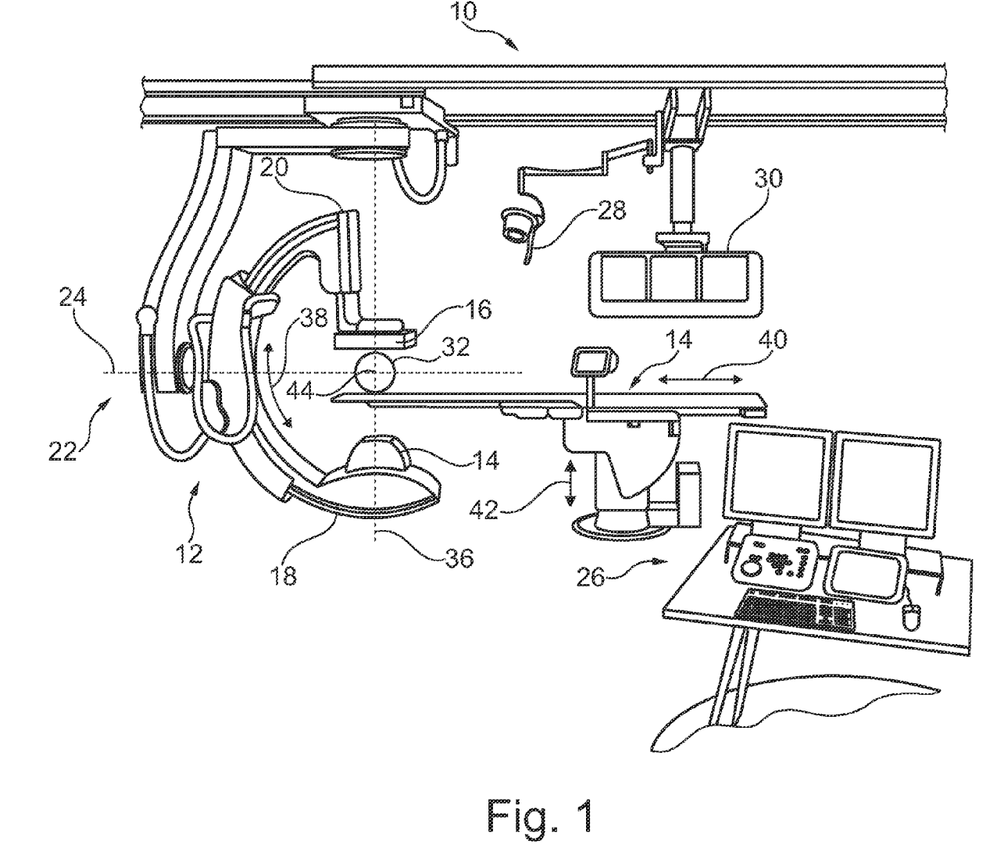
FIG. 1 schematically describes an exemplary embodiment of a C-arm X-ray imaging system according to the present invention.

FIG. 1 shows a C-arm X-ray imaging system 10 comprising a C-arm structure 12 with an X-ray source 14 and an X-ray detector 16 mounted across from the X-ray source, i.e. on opposing ends 18, 20 of the C-arm. Further, a motorized drive 22 for a rotational movement of the C-arm structure is provided. Further, an object support 24 in form of a patient table may be provided. Still further, a control unit 26 is provided.

In addition, FIG. 1 also shows lighting equipment 28 and a display arrangement 30.

The C-arm structure can rotate around an object 32, arranged on the object support 24. The positioning of the patient in relation to the centre of rotation, which forms an ISO-centre, is adjustable. The C-arm structure allows a movement around a horizontal axis 34, as well as a rotational movement around a vertical axis 36. Still further, also an arc-like sliding movement, indicated with double arrow 38, is possible. The movement of the patient table is further indicated with a first double-arrow 40 indicating horizontal movement, and a second double-arrow 42, indicating vertical movement. In order to provide a movement or displacement of the ISO-centre according to the present invention, a displacement, e.g. shift of the table perpendicular to the directions indicated by the two arrows 40 and 42 is provided. Still further, also a rotational movement of a table around a vertical axis is provided, although not further shown. The ISO-centre is indicated by the crossing point of the vertical axis 36 and the horizontal axis 34, which crossing point is indicated with reference numeral 44.

According to the present invention, the C-arm structure is provided to perform a rotational scan around an axis of rotation and around an ISO-centre acquiring a number of X-ray projections in order to generate image data for a reconstructed three-dimensional field of view.

The "transverse" displacement relates to a connection line, which is a straight line, and which is running lateral to the first and the second axis of rotation, i.e. in a cross-wise manner to the first and the second axis of rotation. For example, the first and the second axis of rotation are displaced such that the first and the second field of view are close to each other or close-by, e.g. as adjacent fields of view.

For example, the first and the second axis of rotation are displaced by parallel shifting.

According to another example (not shown), the first and the second axis of rotation are displaced by a transverse shifting, wherein the shifting is having a first perpendicular vector component perpendicular to the two axes of rotation, and a first parallel vector component parallel to the two axes.

According to still another example (not shown), the first and the second axis of rotation are displaced by a transverse shifting, wherein the shifting is having a first perpendicular vector component perpendicular to one of the two axes, and a second perpendicular vector component perpendicular to the other one of the two axes.

According to yet another example (not shown), a combination of a first and a second perpendicular vector component with a parallel vector component is provided.

The first and the second axis of rotation may also be displaced by rotation (not shown).

The first and the second axis of rotation may also be displaced by a shifting parallel and/or perpendicular to one of the two axes and by a rotation (also not shown).

The control unit 26 controls the motorized drive 22 and also causes the rotational movement of the C-arm structure 12. The rotational movements according to the present invention will be described in the following with reference to FIGS. 2 to 6.

Figure 2:
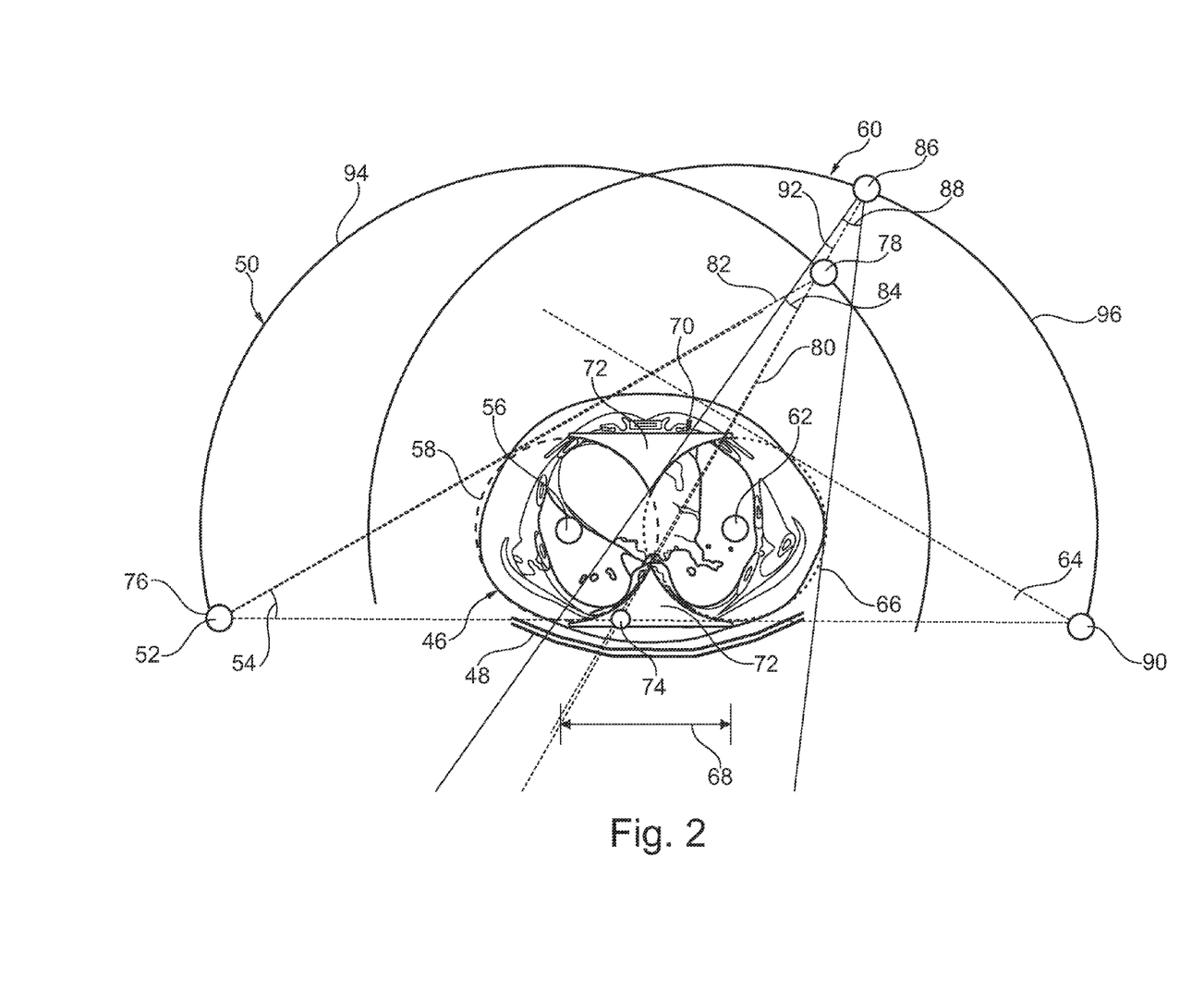
FIG. 2 schematically describes the arrangement of at least two rotational X-ray scans.

FIG. 2 schematically shows an example for a geometric arrangement of different rotational scans. It is noted that the rotational scans are shown in form of a trajectory relating to, for example, the movement path of an X-ray source. For a better understanding, the respective movement of the X-ray source, which happens at the same time due to the mounting of the source and the detector to the opposing ends of the C-arm, is not further shown.

FIG. 2 shows a cross-section 46 of a patient arranged on a support structure 48, the latter representing, for example, the object support 24.

According to the present invention, a first rotational X-ray scan 50 around a first ISO-centre 56 with a first axis of rotation for a first field of view is schematically illustrated by a first trajectory, also indicated with the reference numeral 50. Along the trajectory, a number of X-ray projections are acquired, which, for example, each have a beam with a fan-shaped form in the plane of rotation, covering a first volume of projection for reconstructing a first three-dimensional field of view. For example, for a first point 52, an X-ray projection is indicated with a first angle 54, which angle is defined by the width of the detector in relation to the distance between detector and source.

In FIG. 2, the first axis of rotation is arranged perpendicular to the drawing sheet's surface, through the first ISO-centre. The second axis of rotation is also arranged perpendicular to the drawing sheet's surface, but through the second ISO-centre.

The connection line (not shown) between the first and the second ISO-centre is thus also a connection line between the first and the second axis of rotation.

The X-ray source is moved along the trajectory 50 and is at the same time rotated around the first ISO-centre 56, i.e. a first centre of rotation 56. Thus, when moving the angle 54 in a rotational manner around the centre of rotation 56, a first field of view 58, i.e. first volume of projection 58, indicated by a first dotted circle is provided for reconstructing a first three-dimensional field of view.

A second rotational X-ray scan 60 around a second ISO-centre 62 with a second axis of rotation for a second field of view is indicated with a second trajectory, for which the reference numeral 60 is used, too. The second rotational X-ray scan also comprises a number of X-ray projections with a beam having a fan-shaped form in the plane of rotation covering a second volume of projection for reconstructing a second three-dimensional field of view. The rotation is also performed on an arc around the second ISO-centre 62, i.e. a second centre of rotation 62, for example over at least 140° around an object. For example, the first and second rotations are both performed over at least 140°, for example 180° plus the respective fan angle 54.

A second angle 64 indicates the respective so-to-speak viewing angle, thus providing a second field of view 66, i.e. volume of projection 66, for reconstructing a second three-dimensional field of view. The second volume of projection 66 is indicated with a second dotted circle.

The first and the second centre of rotation 56, 62 are displaced in relation to each other, as indicated with distance double-arrow 68 such that a connection line between the first and the second ISO-centre is arranged transverse to the first and the second axis of rotation.

As a result of the first and second rotational X-ray scans 50, 60, a convex hull 70 is provided as an extended three-dimensional field of view enclosing the first field of view 58 and the second field of view 66, and residual regions 72, which are located inside the convex hull 70, but outside the first and second fields of view 58, 66.

In the example shown in FIG. 2, the rotational movement of the C-arm structure is performed as an arc in form of a circular arc.

According to a further exemplary embodiment, not shown, the rotation is performed with a varying distance of source and/or detector to the centre of rotation, resulting in an elliptically shaped arc, whereas the circular arc is based on a constant and unchanged distance of source and detector to the centre of rotation, respectively.

Independently of the variation of the distance of source and/or detector to the centre of rotation, according to the present invention, the centre of rotation remains fixed. In other words, the C-arm has a (theoretically) fixed ISO-centre for the respective rotational scan. "Theoretically" refers to the fact that a very small movement of the centre of rotation may occur due to bending forces and the like.

The displacement, e.g. shifting and/or rotating, of the first and the second centre of rotation 56, 62 may be provided by displacement of the object support 24 in relation to the C-arm structure 12, or by displacement of the C-arm structure 12 in relation to the object support 24. According to a further example, a combination of a movement of both, the C-arm structure 12 and the object support 24 in relation to each other is provided.

According to a further exemplary embodiment, not further shown, instead of the C-arm structure 12, a so-called O-arm system is provided, where an X-ray detector is arranged opposite to an X-ray source, and an object can be arranged between the two. The movement of source and detector takes place together in a rotational manner.

According to a further example, instead of a C-arm system, two individual robotic arms are provided which are configured to provide a movement like in a C-arm, i.e. a combined movement of X-ray source and detector around a centre of rotation.

In FIG. 2, the first three-dimensional field of view and the second three-dimensional field of view contact each other, for example in an overlapping fashion, as shown.

According to a further example, the first and second fields of view have at least one voxel in common.

According to a still further example, the first and second fields of view may be displaced such that the two dotted circles 58, 66 do not contact each other anymore. However, in such case, the resulting voxel information leads to at least some degree of ambiguity for the pixels in the region between the two circles. Nevertheless, even in such case, a reconstruction of the extended field of view is possible.

For the reconstruction of the first field of view, or first volume of projection, indicated by the dotted circle 58, projection data from the first rotational X-ray scan 50 is used. Thus, all voxels arranged inside the first field of view, i.e. the first dotted circle 58, are seen from all directions along the first rotational X-ray scan 50 and the respective trajectory.

Accordingly, for reconstructing the second field of view, or second volume of projection 66, projection data from the second rotational X-ray scan 60 is used.

For the reconstruction of the voxels in the residual areas 72, projection data from both rotational X-ray scans 50, 60 is used.

For example, for a voxel 74 in the residual area 72, this voxel 74 is seen on a first segment of the first trajectory 50, namely from the so-to-speak starting point, indicated with reference numeral 76, up to a point 78. In the position of the latter, i.e. the point 78, the voxel 74 is still visible, but will not be visible in the next acquisition point, since the voxel 74 is arranged on a first sideline 80 of the respective viewing angle, indicated by the first sideline 80 and a second sideline 82 spanning the viewing angle 84.

However, the voxel 74 is also visible, i.e. detected with the respective projection information, from a point 86 on the second trajectory 60. This is because the voxel 74 is now arranged inside a fan angle 88 of the respective point 86. For the reconstruction, the image data from the first trajectory 50 is used from the starting point 76 up to the point 78, and is then used from the second trajectory 60 from point 86 until the respective end point, indicated by a reference numeral 90.

It must be noted, that when starting from the end point 90 of the second trajectory, when determining a point on the trajectory, up to which the point is visible, a point arranged beyond point 86 will be reached. In other words, in the example shown, an overlapping region exists, in which image data from the two projection trajectories 50 and 60 could be used.

To determine the respective point in the second trajectory, a continuation of a connecting line from the voxel 74 to the second point 78 on the first trajectory can be used, which continuation is indicated with a dotted line segment 92.

The segment of the first trajectory between the first point 76 and the second point 78 is also referred to as a voxel-covering segment 94 of the first trajectory 50. Respectively, the portion of the second trajectory 60 between the point 86 and the end point 90 is referred to as a voxel-covering segment 96 of the second trajectory. The voxel-covering segments 94, 96 are thus segments of the first and/or second rotational X-ray scans, which segments comprise acquisition points for which the voxel that is to be reconstructed is located inside the respective first and/or second field of view, i.e. volume of projection, of the particular acquisition point.

According to a further example, although not further shown, a further rotational X-ray scan is provided in addition to a first and a second rotational X-ray scan. Thus, a further field of view, i.e. further volume of projection for reconstructing a further three-dimensional field of view is provided. For example, this can be provided in a similar, for example, contacting or overlapping manner. For the reconstruction, the respective segments of the trajectories are determined for the voxels outside the fields of view.

Figure 3:
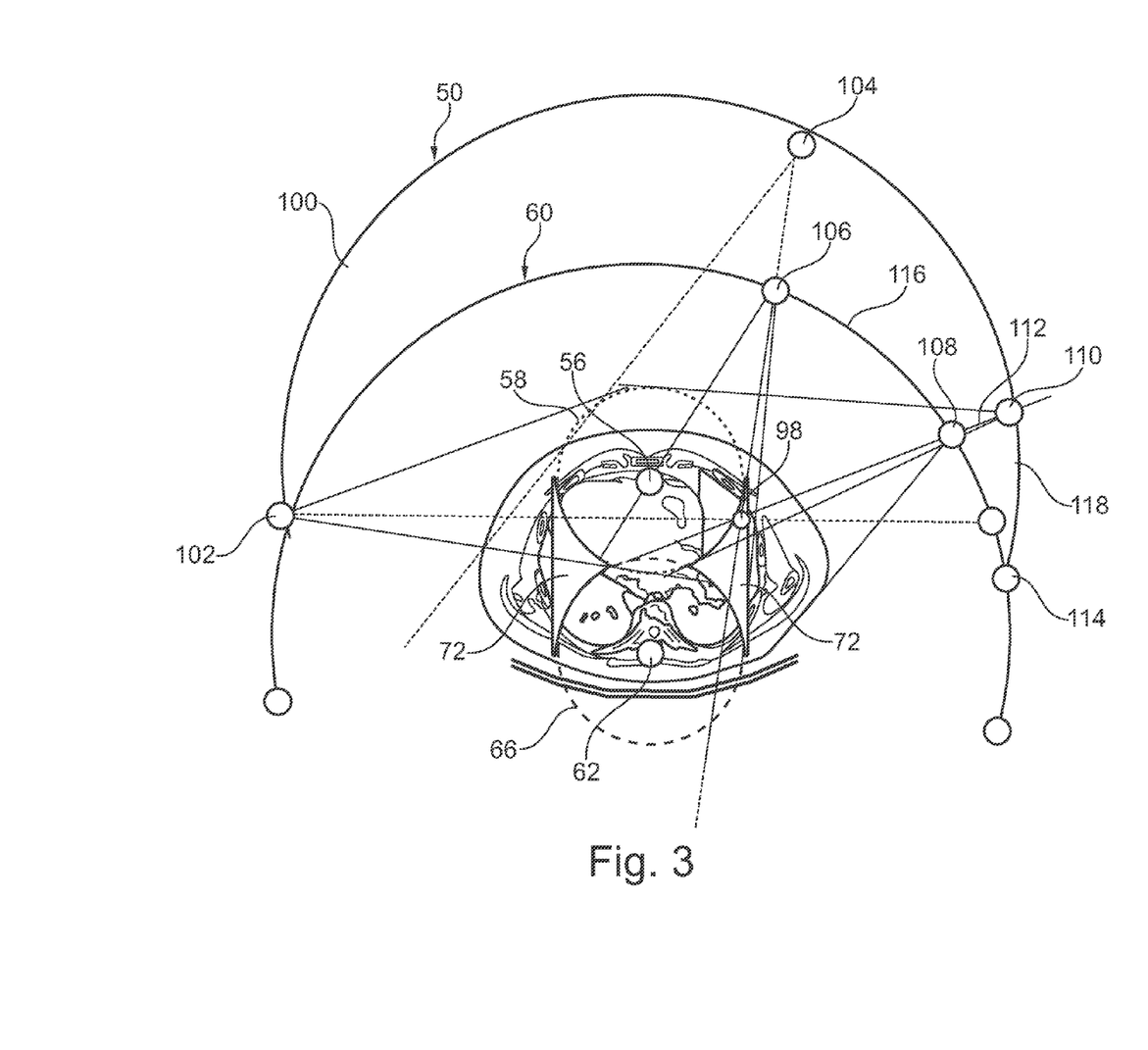
FIG. 3 schematically shows a further embodiment of at least two rotational X-ray scans.
Figure 4:
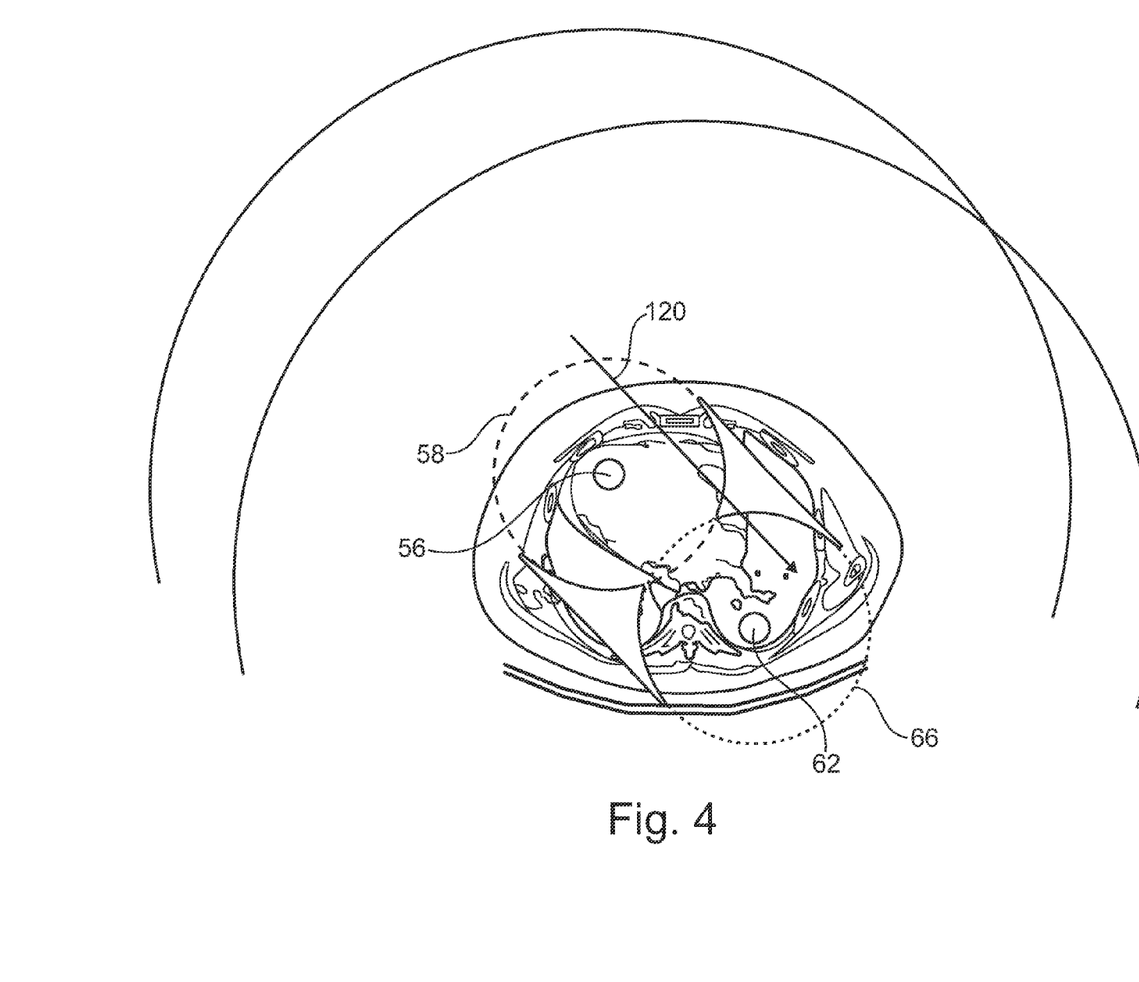
FIG. 4 shows a further exemplary embodiment of two rotational X-ray scans according to the present invention.

The displacement can be provided, for example, in the direction of the chord of the rotation arc, as shown in FIG. 2, or in the direction of an angle bisector of the rotation arc, as shown in FIG. 3, or transverse to the arc, i.e. transverse to the court and transverse to the angle bisector, as shown in FIG. 4.

It is further noted that for the reconstruction of voxels arranged in the residual regions, a plurality of segments from respective trajectories are used.

For example, with reference to FIG. 3, a voxel 98 is reconstructed by using projection data from a first segment 100 of the first trajectory, starting from starting point 102 up to a first segment end point 104. For the further reconstruction, projection data from the second trajectory is used, namely from a point 106 on the second trajectory 60, which is determined by the connection line of the end point 104 on the first trajectory 50, connected with the voxel 98. In the following, image, or projection data from the second trajectory is used up to a second end point 108, which represents the point on the second trajectory, from which the voxel is still visible. Then, it is once again shifted back to the first trajectory by determining a further starting point 110 on the first trajectory 50 by a continuation 112 of the connecting line between the voxel 98 and the point 108 on the second trajectory. Further, projection data from a segment between the second starting point 110 to the end point 114 of the first trajectory 50 is then used for reconstructing the voxel 98. In other words, two different voxel-covering segments of the first trajectory and one covering segment of the second trajectory are used for the reconstruction of the voxel 98.

The voxel-covering segment between the point 106 and the point 108 on the second trajectory 60 is indicated with reference numeral 116, and the segment on the trajectory 50 between the second starting point 110 and the end point 114 is referred to as voxel-covering segment 118.

In FIG. 3, the displacement is shown in a vertical manner with respect to the orientation of the drawing from the top to the bottom, wherein FIG. 4 schematically shows a transverse displacement, indicated with arrow 120. The determination of a respective voxel is not further shown in FIG. 4, but can be easily understood on behalf of the above provided explanation. Further, the displacement is shown in an overlapping result of circular cross-sections in trans-axial directions defining the first and second field of view (volume of projection). The width of the first and second three-dimensional fields of view diameter is defined by a width of the effective radiation beam at the centre of rotation, which effective radiation beam is the part of the X-ray beam hitting the detector and used for the acquisition of the image data. The circular cross-section has a diameter. The displacement can be equal or less the diameter. Thus, the circular cross-sections contact each other, or at least have one voxel or more in common.

Of course, the present invention is also applicable to a displacement of more than the diameter.

It is further noted that the above given explanation refers to an example of a circular arc movement, i.e. a circular arc trajectory for the first and second X-ray scans. However, the rotational scans can also be performed on differently shaped arcs, for example on elliptical arcs. In such cases, of course, the resulting volumes of projection would not be represented by circles, but rather by elliptical or otherwise shaped forms.

Figure 5:
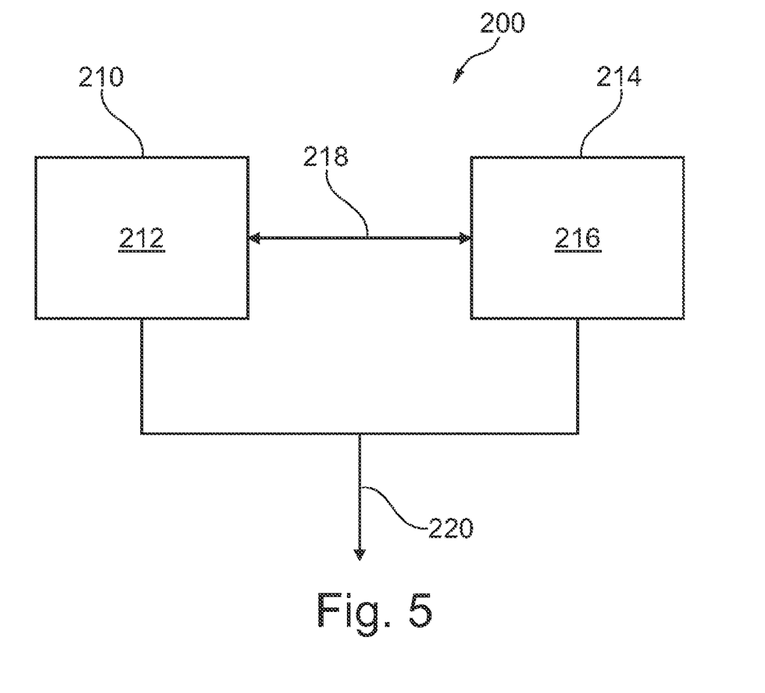
FIG. 5 schematically illustrates basic method steps of a method for acquiring three-dimensional image data of an object according to the present invention.

FIG. 5 shows basic steps of a method 200 for acquiring 3D X-ray image data of an object, comprising the following steps: In a first step 210, a first rotational X-ray scan 212 around a first ISO-centre is performed.

For example, the first rotational X-ray scan is performed with a number of X-ray projections, which each have a beam with a fan-shaped form in the plane of rotation covering a first field of view (volume of projection) for reconstructing a first three-dimensional field of view, wherein the rotation is performed on an arc around the first ISO-centre over at least 140° around an object.

In a second step 214, at least a second rotational X-ray scan 216 is performed around a second ISO-centre.

For example, the second rotational X-ray scan is performed with a number of X-ray projections with a beam having a fan-shaped form in the plane of rotation covering a second field of view (volume of projection) for reconstructing a second three-dimensional field of view, wherein the rotation is performed on an arc around a second centre of rotation over at least 140° around an object.

The first and the second centre of rotation are displaced in relation to each other, as indicated with double-arrow 218, such that a connection line between the first and the second ISO-centre is arranged transverse to the first and the second axis of rotation.

An arrow 220 indicates the further use of the thus acquired image data.

For example, the first and second fields of view have at least one voxel in common, or contact each other.

The first and second rotational scans are performed with a static ISO-centre each.

According to a further example, a convex hull is provided as an extended three-dimensional field of view enclosing the first field of view and the second field of view and residual regions, which residual regions are located inside a convex hull, but outside the first and second fields of view.

For example, the residual regions are provided with a double-wedge-like form. The residual regions may also be referred to as residual areas.

Figure 6:
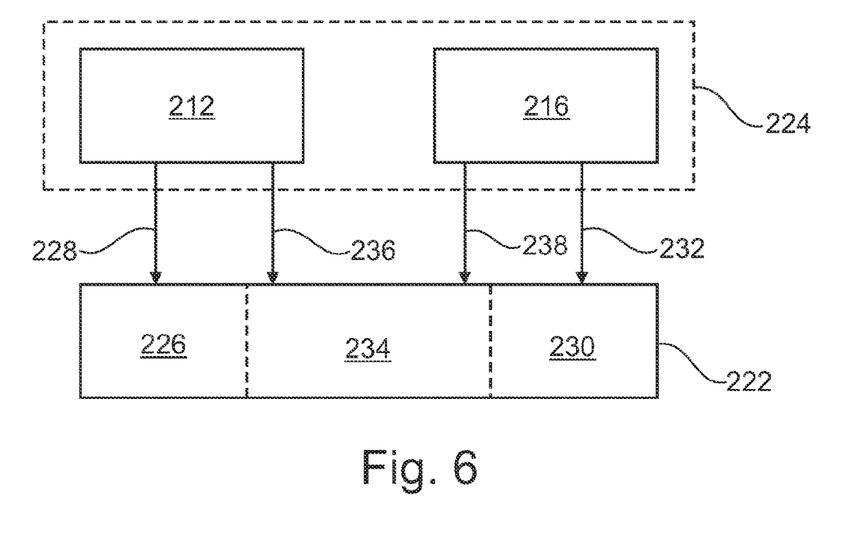
FIG. 6 schematically shows a further example of a method according to the present invention.

FIG. 6 shows a further embodiment of a method according to the present invention, in which a reconstruction step 222 is provided in addition to image acquisition steps, enclosed a dotted rectangular 224. For a reconstruction 226 of the first field of view, projection data from the first rotational X-ray scan is used, which projection data is indicated with an arrow 228. For a reconstruction 230 of the second field of view, projection data from the second rotational X-ray scan is used, as indicated by arrow 232. For a reconstruction 234 of the residual regions, projection data from at least one part of the first field of view is used, as indicated with reference numeral 236, and also projection data from at least one part of the second field of view is used, as indicated with arrow 238.

According to a further aspect, it is also possible to use the projection data of the respective other arc to improve the signal-to-noise-ratio (SNR).

For reconstructing a voxel inside residual regions, projection from voxel-covering segments is used, wherein the voxel-covering segments are segments of the first and/or second rotational X-ray scans, which segments comprise acquisition points from which the voxel that is to be reconstructed is located inside the respective field of view of the particular acquisition point.

For example, for reconstructing a voxel inside the residual regions, differentiating back-projected projection data along the voxel-covering segments is used.

According to the present invention, an extended field of view for 3D X-ray imaging is provided without the need of a large detector or other mechanical means.

As a result, for example when referring to FIG. 2, an increased field of view of approximately 14% compared to two circles is provided $(\pi r^2 + 4r^2)/(2\pi r^2) \approx 1.14$.

Thus, the extended field of view is applicable for a number of different applications, providing improved application situations, such as for example, for liver TACE, spine interventions, uterine artery embolization, imaging of both femoral arteries at a time.

The extended field of view is provided with multiple arcs. Thus, the present invention aims at enabling a bigger field of view by scanning two or more arcs with shifted ISO-centre in one, i.e. a single reconstruction. Three candidate solutions are provided:

First, two independent FDK reconstructions with smooth feathering are provided: Two reconstructions are performed separately and then stitched together by smooth blending. As an advantage, this solution is insensitive to inter-scan motion. However, truncation artefacts might be present in both reconstructions.

Second, a modification of a Defrise-Clack reconstruction algorithm for multiple arcs is provided. This means an FBP into the same volume. As an advantage, the field of view can be increased up to 14% compared to two circles. However, truncation problems due to long range filtering in projections may still occur. Further, inter-scan motion may introduce artefacts.

Third, a modification of BPF reconstruction algorithm for multiple arcs is provided. The differentiated projections from both circular arcs are back-projected into the same volume. The inverse Hilbert transform is then applied to this single volume. As an advantage, the field of view is increased up to 14% with exact reconstruction if the extended field of view is non-truncated along the PI-lines. However, inter-scan motion may introduce artefacts.

According to a further example, an iterative reconstruction is provided.

As an advantage, a larger field of view is provided, for example a body surface in the field of view for needle path planning and tracking, complete liver imaging, or the like.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A C-arm X-ray imaging system, provided to acquire extended three-dimensional images of an object, the imaging system comprising:
   a C-arm structure with an X-ray source and an X-ray detector mounted across from the X-ray source;
   a motorized drive for a rotational movement of the C-arm structure; and
   a control unit; wherein
   the C-arm structure is provided to perform a rotational scan around an axis of rotation and around an ISO-center acquiring a number of X-ray projections for generating image data of a reconstructed three-dimensional field of view;
   the control unit is configured to control the motorized drive; and
   the control unit is configured to cause the rotational movement of the C-arm structure to perform:
      a first rotational X-ray scan around a first ISO-center with a first axis of rotation for a first field of view; and
      a second rotational X-ray scan around a second ISO-center with a second axis of rotation for a second field of view;
   the first and the second ISO-center are displaced in relation to each other such that a connection line between the first and the second ISO-centers is arranged transverse to the first and the second axes of rotation; and
   the control unit is configured to provide a convex as an extended three-dimensional field of view enclosing the first field of view and the second field of view and residual region, which residual regions are located inside the convex hull, but outside the first and second fields of view.

2. The C-arm X-ray imaging system according to claim 1, wherein:
   the C-arm structure is configured to perform the first rotational X-ray scan with a first trajectory and the second rotational X-ray scan with a second trajectory displaced to the first trajectory; and
   the first and the second trajectory have the same trajectory shape.

3. The C-arm X-ray imaging system according to claim 1, wherein the control unit is configured to cause the rotational movement of the C-arm structure to perform the rotational scans such that the first and the second field of view contact each other.

4. The C-arm X-ray imaging system according to claim 1, wherein the first and second axes of rotation are displaced parallel to each other such that the connection line between the first and the second ISO-centers is arranged perpendicular to the first and the second axes of rotation.

5. The C-arm X-ray imaging system according to claim 1, wherein the C-arm structure is provided to perform the first and the second rotational scans as a circular arc respectively.

6. The C-arm X-ray imaging system according to claim 1, wherein:
   the control unit is configured to use projection data from the first rotational X-ray scan for a reconstruction of the first field of view and projection data from the second rotational X-ray scan for a reconstruction of the second field of view; and
   the control unit is configured to use projection data from the first field of view and projection data from the second field of view for a reconstruction of the residual regions.

7. The C-arm X-ray imaging system according to claim 1, wherein:
   the control unit is configured to use projection data from voxel-covering segments for reconstructing a voxel inside the residual regions, and
   the voxel-covering segments are segments of the first and/or second rotational X-ray scans, which segments comprise acquisition points for which the voxel that is to be reconstructed is located inside the respective first and/or second field of view of a particular acquisition point.

8. A method for acquiring three-dimensional (3D) X-ray image data of an object, the method comprising:
   a) performing a first rotational X-ray scan comprising a first field of view around a first ISO-center;
   b) performing a second rotational X-ray scan comprising a second field of view around a second ISO-center; wherein:
   the first and the second ISO-centers of rotation are displaced in relation to each other such that a connection line between the first and the second ISO-center is arranged transverse to the first and the second axes of rotation; and
   c) providing a convex hull is provided as an extended three-dimensional field of view enclosing the first field of view and the second field of view and residual regions, which residual regions are located inside the convex hull, but outside the first and second fields of view.

9. The method according to claim 8, wherein:
   the first rotational X-ray scan in step a) is performed with a first trajectory;

the second rotational X-ray scan in step b) is performed with a second trajectory displaced to the first trajectory; and the first and the second trajectory have the same trajectory shape.

10. The according to claim 8, wherein at least one of the following group is provided:
   i) the first and the second ISO-center are displaced such that the first and second fields of view contact each other;
   ii) the first and second axes of rotation are displaced parallel to each other such that the connection line between the first and the second ISO-centers is arranged perpendicular to the first and the second axes of rotation; and
   iii) the first and the second rotational scans are performed as a circular arc respectively.

11. The method according to claim 8, wherein:
   for a reconstruction of the first field of view, projection data from the first rotational X-ray scan is used;
   a reconstruction of the second field of view, projection data from the second rotational X-ray scan is used; and
   for a reconstruction of the residual regions, projection data from the first field of view and projection data from the second field of view used.

12. The method according to claim 8, wherein:
   for reconstructing a voxel inside the residual regions, projection data from voxel-covering segments is used; and
   the voxel-covering segments are segments of the first and/or second rotational X-ray scans, which segments comprise acquisition points for which the voxel that is to be reconstructed is located inside the respective first and/or second field of view of a particular acquisition point.

13. The method according to claim 12, wherein for reconstructing the voxel inside the residual regions, differentiated back-projected projection data along the voxel-covering segments is used.

14. A non-transitory computer readable storage medium storing instructions that when executed by a processor perform the method defined by claim 8.

15. The imaging system of claim 1, wherein:
   the first field of view is a region of the object through which every X-ray projection of the first rotational X-ray scan passes,
   the second field of view is another region of the object through which every X-ray projection of the second rotational X-ray scan passes, and
   the control unit uses X-ray projection data solely from the first rotational X-ray scan for a reconstruction of the first field of view within the extended three-dimensional field of view and uses X-ray projection data solely from the second rotational X-ray scan for a reconstruction of the second field of view within the extended three-dimensional field of view.

16. The imaging system of claim 15, wherein:
   the residual regions are regions of the object through which:
      some, but not all, X-ray projections of the first rotational X-ray scan pass, and
      some, but not all, X-ray projections of the second rotational X-ray scan pass, and
   the control unit uses X-ray projection data from each of the first and second rotational X-ray scans to produce a reconstruction of the residual regions.

17. The imaging system of claim 1, wherein each Cartesian coordinate of a vector drawn from the first ISO-center to the second ISO-center having a non-zero magnitude is orthogonal to each of the first and second axes of rotation.

* * * * *